United States Patent [19]
Lee et al.

[11] Patent Number: 6,031,119
[45] Date of Patent: Feb. 29, 2000

[54] POLYALKYLENE GUANIDINE SALTS OR POLYALKYLENE BIGUANIDINE SALTS HAVING A BRANCHED SILANE COMPOUND, METHOD FOR PREPARING SAME AND USES THEREOF

[75] Inventors: Byung-Hyoung Lee; Woo-Sun Kim; Young-Jun Kim; Sang-Gu Bang; Kwang-Min Lim; Sang-Rak Choi; Keum-Chan Joo, all of Taejon, Rep. of Korea

[73] Assignee: Yukong Limited, Seoul, Rep. of Korea

[21] Appl. No.: 08/889,514

[22] Filed: Jul. 8, 1997

[51] Int. Cl.$^7$ .................................. A61K 31/155
[52] U.S. Cl. ......................... 556/410; 514/63; 556/412; 556/413; 556/423; 556/424
[58] Field of Search ................................. 556/413, 410, 556/412, 423, 424; 514/63

[56] References Cited

U.S. PATENT DOCUMENTS 5,283,310  2/1994  Armand et al. ............................ 528/30

*Primary Examiner*—Peter O'Sullivan
*Attorney, Agent, or Firm*—Abelman, Frayne & Schwab

[57] ABSTRACT

Polyalkylene guanidine salts or polyalkylene biguanidine salts having a branched silane compound of formula I show excellent antimicrobial activity and can be applied to various materials including fibers, wood, paper, glass, resins and metals:

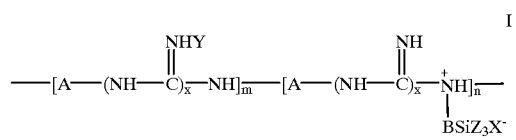

wherein A is oxyethylene, oxypropylene, oxybutylene, oxystyrene, diphenylsulfone, diphenyl sulfide or alkylamide, which repeating number is 1 to 100,000, or straight or branched alkyl chain containing 1 to 20 carbon atoms;

Y represents a blank, HCl, HBr, HI, $HNO_3$, acetic acid, benzoic acid, dehydroacetic acid, propionic acid, gluconic acid, sorbic acid, phosphoric acid, fumaric acid, maleic acid, carbonic acid, sulfuric acid or para-toluene sulfonic acid;

B is a straight or branched alkyl chain containing 0 to 20 carbon atoms;

Z is an alkoxy group such as methoxy, ethoxy, propoxy, isopropoxy, butoxy, pentoxy, hexoxy, octoxy or decoxy, chloride, bromide, iodide, acetate, sulfate, or paratoluenesulfonate;

X is chloride, bromide, iodide, acetate, sulfate, paratoluenesulfonate, methoxy, ethoxy, propoxy, isopropoxy, butoxy, pentoxy, hexoxy, octoxy, or decoxy;

x is 1 or 2;

m is an integer of 0 or more; and n is an integer of 1 or more with a proviso that the ratio of m to n ranges from 0.01 to 100 in case of m+n=4 and when m is 0, n is an integer of 4 or more.

7 Claims, No Drawings

POLYALKYLENE GUANIDINE SALTS OR POLYALKYLENE BIGUANIDINE SALTS HAVING A BRANCHED SILANE COMPOUND, METHOD FOR PREPARING SAME AND USES THEREOF

BACKGROUND OF THE INVENTION

1. Field of the Invention

The present invention relates to novel polyalkylene guanidine salts or polyalkylene biguanidine salts having a branched silane compound and a method for preparing them. Also, the present invention is concerned with uses of polyalkylene guanidine salts or polyalkylene biguanidine salts having a branched silane compound as antimicrobial agents.

2. Description of the Prior Art

Generally, antimicrobial agents are referred to as functional substances which are able to prevent a human being or other objects from being infected by microorganisms including bacteria, fungi and pathogens. Such function comes from antimicrobial agents which are applied to substances such as fibers, wood, paper, glass, resins and metals and thus protect them against the microorganisms. For example, the antimicrobial agents for fibers include organic compounds such as quaternary ammonium salts (J. Appl. Polym. Sci., Vol. 37, no. 10, 1989, pp 2837–2843), quaternary ammonium silane salts (Japanese Patent Laid-Open Sho 61-15188), various higher organic acids, chitosans (deacylated chitin) (Japan, Dye Industry Vol. 41, no. 4, 1993, pp 9–15), chlorhexidine, polyhexamethylene biguanidine salts (Japanese Patent Laid-Open Hei 7-82663), acrylonitrile copper sulfate complexes and inorganic compounds such as Ag-, Cu- or Zn-impregnated zeolite. These antimicrobial agents for fibers are required to exhibit a safety for the human being, stability and wash fastness for fibers, in addition to being of excellent antimicrobial activity.

Polyhexamethylene guanidine salts or polyalkylene biguanidine salts, well-known antimicrobial agents having a low toxicity, are widely utilized for water treatment such as in swimming pools and spas. The high solubility of said polyhexamethylene guanidine salts or polyhexamethylene biguanidine salts in water makes them elute readily from the materials, leading to the deterioration of the fastness. This is believed to be attributed to the low adhesiveness of the agents to the material, such as fibers, wood, paper, glass, resins and metals.

SUMMARY OF THE INVENTION

The intensive and thorough research of the present inventors for solving the above problems encountered in prior arts results in the development of novel compound which is superior in adhesiveness to various materials and in antimicrobial activity. Based on this fact, the invention is developed and accomplished.

Therefore, it is an objective of the present invention to provide novel polyalkylene guanidine salts or polyalkylene biguanidine salts having a branched silane compound for an antimicrobial use for various natural fibers, such as cotton, silk, wool, hemp and etc., synthetic fibers, such as rayon, polyester, nylon, acryl, acetate, polyolefin and etc., wood, paper, glass, various natural and synthetic resins, and various metals.

It is another objective of the present invention to provide a method for preparing the polyalkylene guanidine salts or polyalkylene biguanidine salts having a branched silane compound.

It is still another objective of the present invention to provide the use of the polyalkylene guanidine salts or polyalkylene biguanidine salts having a branched silane compound as an antimicrobial agent.

It is a further objective of the present invention to provide an antimicrobial composition comprising the polyalkylene guanidine salts or polyalkylene biguanidine salts having a branched silane compound as an active ingredient.

The present polyalkylene guanidine salts or polyalkylene biguanidine salts having a branched silane compound for accomplishing the above objectives are represented by the following formula I:

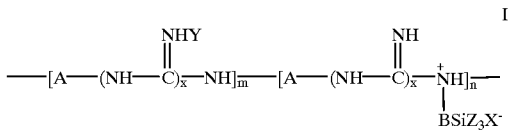

wherein A is oxyethylene, oxypropylene, oxybutylene, oxystyrene, diphenylsulfone, diphenylsulfide or alkylamide, with a repeating number of 1 to 100,000, or straight or branched alkyl chain containing 1 to 20 carbon atoms;

Y is nothing or represents, HCl, HBr, HI, HNO$_3$, acetic acid, benzoic acid, dehydroacetic acid, propionic acid, gluconic acid, sorbic acid, phosphoric acid, fumaric acid, maleic acid, carbonic acid, sulfuric acid or paratoluene sulfonic acid;

B is a straight or branched alkyl chain containing 0 to 20 carbon atoms;

Z is an alkoxy group selected from the group consisting of methoxy, ethoxy, propoxy, isopropoxy, butoxy, pentoxy, hexoxy, octoxy or decoxy, chloride, bromide, iodide, acetate, sulfate, or paratoluenesulfonate;

X is chloride, bromide, iodide, acetate, sulfate, paratoluenesulfonate, methoxy, ethoxy, propoxy, isopropoxy, butoxy, pentoxy, hexoxy, octoxy, or decoxy;

x is 1 or 2;

m is an integer of 0 or more; and n is an integer of 1 or more with a proviso that the ratio of m to n ranges from 0.01 to 100 in case of m+n=4 and when m is 0, n is an integer of 4 or more.

According to an aspect of the present invention, there is provided a method for preparing the polyalkylene guanidine salts or polyalkylene biguanidine salts having a branched silane compound represented by the formula I, comprising reacting polyalkylene guanide or polyalkylene biguanide, or polyalkylene guanidine salts or polyalkylene biguanidine salts, both represented by the following formula II:

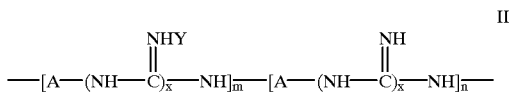

wherein A, Y, x, m and n each are as defined above, with silane compounds, represented by the following formula III:

wherein X, B and Z each are as defined above, in the presence or absence of a catalyst and a solvent with stirring at a temperature of 0° C. or more.

According to another aspect of the present invention, there is provided an antimicrobial agent composition comprising 0.1 to 80% by weight of the polyalkylene guanidine salts or polyalkylene biguanidine salts having a branched silane compound as an active ingredient in water or an organic solvent having a boiling point of 25 to 300° C.

DETAILED DESCRIPTION OF THE INVENTION

The present invention pertains to novel polyalkylene guanidine salts or polyalkylene biguanidine salts having a branched silane compound suitable for antimicrobial protection for various materials, represented by the following formula I:

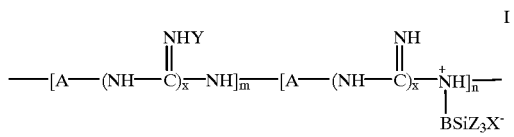

wherein A is oxyethylene, oxypropylene, oxybutylene, oxystyrene, diphenylsulfone, diphenyl sulfide or alkylamide, with a repeating number of 1 to 100,000, or straight or branched alkyl chain containing 1 to 20 carbon atoms;

Y is nothing or represents, HCl, HBr, HI, $HNO_3$, acetic acid, benzoic acid, dehydroacetic acid, propionic acid, gluconic acid, sorbic acid, phosphoric acid, fumaric acid, maleic acid, carbonic acid, sulfuric acid or para-toluene sulfonic acid;

B is a straight or branched alkyl chain containing 0 to 20 carbon atoms;

Z is an alkoxy group such as methoxy, ethoxy, propoxy, isopropoxy, butoxy, pentoxy, hexoxy, octoxy or decoxy, chloride, bromide, iodide, acetate, sulfate, or paratoluenesulfonate;

X is chloride, bromide, iodide, acetate, sulfate, paratoluenesulfonate, methoxy, ethoxy, propoxy, isopropoxy, butoxy, pentoxy, hexoxy, octoxy or decoxy;

x is 1 or 2;

m is an integer of 0 or more; and n is an integer of 1 or more with a proviso that the ratio of m to n ranges from 0.01 to 100 in case of m+n=4 and when m is 0, n is an integer of 4 or more.

The novel compound (I) of the present invention is prepared by introducing a silane compound represented by the following formula III:

$$XBSiZ_3 \qquad \text{III}$$

wherein X, B and Z each are as defined above, into a polyalkylene guanide or polyalkylene biguanide or polyalkylene guanidine salts or polyalkylene biguanidine salts, represented by the following formula II:

wherein A, Y, x, m and n are as defined above.

Exhibiting a greatly broad spectrum of germicidities against various microorganisms, the polyhexamethylene guanidine salts or polyalkylene biguanidine salts are far superior to quaternary ammonium salts in antibacterial and antifungal activity. The silane compound is introduced as a bridging agent to the guanidine or biguanidine group of polyalkylene guanides or polyalkylene biguanides which are water-soluble high molecular weight compounds, and enables the active compound to adhere fast to various materials. Thus its introduction into the active compound can solve the problem of the conventional antimicrobial agents, for example, elution from materials when washing.

Since the bridging agent is harmless to a human being, it can be used without limitation in safety. In addition, the chemical modification with the bridging agent allows the antimicrobial active ingredient to chemically bond to or coat on various materials only by a very simple treatment.

When the compound of formula I is applied for fibers, its wash fastness is good under ordinary washing conditions. For example, the fibers which are treated with the antimicrobial agent of the present invention show as much as 99% or more of the original antimicrobial activity after they are washed 50 times. In addition, the compound is not eluted from the fibers even under severe conditions including strong acid or strong alkali, retaining its antimicrobial activity against various microorganisms. Hence, the antimicrobial compound of the present invention shows excellent performance compared with conventional ones for fibers.

Conventional quaternary ammonium silane salts are a product of the reaction in which tertiary amine reacts with silane compound at an equivalent ratio of 1:1. In contrast, the equivalent ratio of the silane compound to the guanidine or biguanidine function group showing the antimicrobial activity in the compound of formula I, is largely reduced, so that it is economically favorable. In addition, the conventional quaternary ammonium silane salts have problem in long term storage and stability, because the trialkoxysilane is hydrolyzed during transport or upon processing fibers and silanol groups are condensed and precipitated. On the contrary, the antimicrobial compound (I) of the present invention is greatly improved in stability and processability by strengthening its performance. The reason for such long term stability is that, since the silane groups are intermittently bonded to the guanidine or biguanidine groups in the compound (I) of the present invention, the degree of freedom of the silane groups is limited so that the reaction probability therebetween is exceptionally reduced.

In detailed chemical terms, the polyalkylene guanidine salts or polyalkylene biguanidine salts having a branched silane compound of formula I is prepared by reacting the polyalkylene guanide or polyalkylene biguanide, or polyalkylene guanidine salts or polyalkylene biguanidine salts of formula II with the silane compound of formula III at a temperature of 0° C. or more with stirring, in which the above reaction may be accomplished in the presence or absence of a catalyst and solvent:

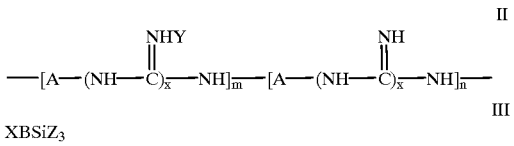

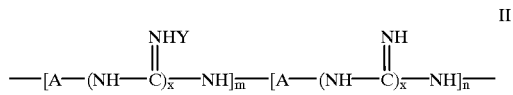

wherein A, B, X, Y, Z, x, m and n each are as defined above.

This nucleophilic substitution reaction can be done either in the presence of a lower alcohol, such as methanol, ethanol, propanol, butanol, pentanol or hexanol, an organic acid, such as formic acid, acetic acid or propionic acid, an aromatic solvent, such as benzene, toluene or xylene, a polar solvent, such as dimethyl sulfoxide, dimethylformamide, N-methylpyrrolidone, tetrahydrofuran, petroleum ether, dimethoxyethane or nitromethane, or a halogenic solvent, such as dichloromethane, dichloroethane, chloroform, tetrachlorocarbon or trichlorobenzene, or in the absence of any solvent.

The antimicrobial compound of formula I can be obtained in an amount as much as the equivalent of the silane compound added which acts as an electrophile for the polyalkylene guanide or polyalkylene biguanide or polyalkylene guanidine salts or polyalkylene biguanidine salts of formula II.

It is preferred that the silane compound is added at an amount of 0.01 to 1 equivalent to the guanidine or biguanidine group. For example, if the equivalent is less than 0.01, the resulting antimicrobial compound is poor in adhesion to the material. On the other hand, when exceeding 1 equivalent, it is uneconomic.

Useful are metal alkoxy compounds, such as alkoxides of alkali metal and alkoxides of alkali earth metal, metal hydride compounds, such as hydrides of alkali metal and hydrides of alkali earth metal, zero equivalent alkali or alkali earth metals, amines, such as pyridine, dimethylaminopyridine and trialkyl amine, and alkylid of alkali metal.

The reaction temperature is 0° C. or more, preferably 10 to 200° C. For example, if the nucleophilic substitution reaction is carried out at lower than 0° C., the reaction rate is slow. On the other hand, if the reaction is carried out at higher than 200° C., by-products are generated.

In accordance with one aspect of the present invention, an antimicrobial composition which is applicable to various materials can be prepared by mixing 0.1 to 80% by weight of the antimicrobial active compound of formula I with 99.9 to 20% by weight of water or an organic solvent having a boiling point of 25 to 300° C. More than 80% by weight of the compound of formula I gives rise to increasing the viscosity of the resulting composition, deleteriously affecting the processability thereof.

Preferred organic solvents for this purpose include lower alcohols, such as methanol, ethanol, propanol, butanol, pentanol and hexanol, organic acids, such as formic acid, acetic acid and propionic acid, aromatic solvents, such as benzene, toluene and xylene, polar solvents, such as dimethylsulfoxide, dimethylformamide, N-methylpyrrolidone, tetrahydrofuran, petroleum ether, dimethoxyethane and nitromethane, and halogenic solvents, such as dichloromethane, dichloroethane, chloroform, tetrachlorocarbon and trichlorobenzene.

The above antimicrobial composition in water or the organic solvent may be diluted to $1 \times 10^{-5}$ to 50% by volume by admixture with water, to give a diluted antimicrobial composition. Various materials can be endowed with antimicrobial activity by immersing them in the diluted composition, followed by drying, or by spraying the diluted composition on them, followed by drying.

Antimicrobial assay of the antimicrobial materials shows that the compound of formula I is far superior to the conventional antimicrobial agents (quaternary ammonium silane salts) in antimicrobial activity, and the wash fastness experiment shows that the compound of the present invention retains its antimicrobial activity for a longer time even after repetitive washing.

A better understanding of the present invention may be obtained through the following examples which are set forth to illustrate, but are not to be construed as the limit of the present invention.

Examples I to III each contain a description of the preparation of the compound of formula I while Example I is a compound (hereinafter referred to as "PAGS-1") wherein A is $(CH_2)_6$, x is 1, m/n is 5, B is $CH_2CH_2CH_2$, Z is OEt, X is Cl and Y represents a blank, Example II for a compound (hereinafter referred to as "PAGS-2") wherein A is $(CH_2)_6$, x is 1, m/n is 10, B is $CH_2CH_2CH_2$, Z is OEt, X is Cl and Y is Cl, and Example III for a compound (hereinafter referred to as "PAGS-3") wherein A is $(CH_2)_6$, x is 2, m/n is 5, B is $CH_2CH_2CH_2$, Z is OEt, X is Cl and Y represents a blank.

The antimicrobial assay of the PAGS compounds obtained in Examples I to III was tested in Example IV, and the antimicrobial activity comparison between PAGS-1 of Example I and a quaternary ammonium silane salt was tested in Example V.

Example VI describes the preparation of an antimicrobial PAGS solution, whose stability is compared with that of a quaternary ammonium silane salt.

Example VII describes the preparation of antimicrobial material sample by the treatment of materials with antimicrobial PAGS solution.

Examples VIII to X contemplate for the properties of antimicrobial material samples, their antimicrobial activities in Example VIII, their wash fastness in Example IX, and their durability against strong acid or strong alkali in Example X.

EXAMPLE I

Preparation of Polyalkylene Guanidine Salt Having a Branched Silane Compound (PAGS-1)

In a 2500 ml round-bottom flask equipped with a magnetic stirrer and a condenser, polyhexamethyleneguanidine (141.2 g), ethanol solvent (524 g), and chloropropyltriethoxysilane (48.1 g) were placed and then, heated at a temperature of 80° C. or less for 2 hrs in an oil bath with stirring. The progress of reaction was monitored by thin layer chromatography (TLC).

After completion of the reaction, the reaction solution was cooled to room temperature, then added with ethanol solvent (200 g) and stirred for 10 min. Using a Buchner funnel, the precipitates formed were filtered off to obtain a solution of PAGS-1 in ethanol.

The solvent was removed by vacuum drying, to give PAGS-1: Yield 95%.

$^1$H-NMR and TLC showed that un-reacted chloropropyl triethoxy silane compound did not remain in the product.

$^1$H-NMR 200 MHz($D_2O$): δ3.60 ppm(q, 2H, J=7.18 Hz), 3.12 ppm(t, 15H, 7.34 Hz), 2.54 ppm(t, 5H, J=6.38 Hz), 1.65–1.43 ppm(br s, br s 40H), 1.13 ppm(t, 3H, J=6.92 Hz), 0.53 ppm(t, 2H, J=8.82 Hz).

Conditions of TLC analysis:

Rf value of chloropropyltriethoxysilane; 0.9 (Developing solution; n-hexane/ethyl acetate=4/1).

There is no un-reacted chloropropyltriethoxysilane compound on thin layer chromatography after completion of the reaction.

EXAMPLE II

Preparation of Polyalkylene Guanidine Salt Having a Branched Silane Compound (PAGS-2)

In a 2500 ml round-bottom flask equipped with a magnetic stirrer and a condenser, polyhexamethyleneguanidine (141.2 g), ethanol solvent (614 g) and chloropropyltriethoxysilane (24.1 g) were placed and then, heated at a temperature of 80° C. or less for 2 hrs in an oil bath with stirring. The progress of reaction was monitored by thin layer chromatography (TLC).

After completion of the reaction, the reaction solution was cooled to room temperature, then added with ethanol solvent (100 g) and stirred for 10 min. Then 35% aqueous hydrochloric acid solution (93.8 g) is added at room temperature and stirred for 10 min. Using a Buchner funnel, the precipitates formed were filtered off to obtain a solution of PAGS-2.

The solvent was removed by vacuum drying, to give PAGS-2: Yield 97%.

$^1$H-NMR and TLC analysis showed that un-reacted chloropropyltriethoxysilane compound did not remain in the product.

$^1$H-NMR 200 MHz($D_2O$) δ3.60 ppm(q, 2H, J=7.18 Hz), 3.12 ppm(t, 30H, 7.34 Hz), 2.54 ppm(t, 10H, J=6.38 Hz), 1.65–1.43 ppm(br s, br s 80H), 1.13 ppm(t, 3H, J=6.92 Hz), 0.53 ppm(t, 2H, J=8.82 Hz).

Conditions of TLC analysis:

Rf value of chloropropyltriethoxysilane; 0.9 (Developing solution; n-hexane/ethyl acetate=4/1).

There is no un-reacted chloropropyltriethoxysilane compound on thin layer chromatography after completion of the reaction.

EXAMPLE III

Preparation of Polyalkylene Biguanidine Having a Branched Silane Compound (PAGS-3)

In a 2500 ml round-bottom flask equipped with a magnetic stirrer and a condenser, polyhexamethylene biguanidine (183.3 g) ethanol solvent (792 g) and chloropropyltriethoxysilane (48.1 g) were placed and then, heated at a temperature of 80° C. or less for 2 hrs in an oil bath while stirring. The progress of reaction was monitored by thin layer chromatography (TLC).

After completion of the reaction, the reaction solution was cooled to room temperature, then added with ethanol solvent (100 g) and stirred for 10 min. Using a Buchner funnel, the precipitates formed were filtered off to obtain a solution of PAGS-3 in ethanol.

The solvent was removed by vacuum drying, to give PAGS-3: Yield 94%.

$^1$H-NMR and TLC analysis showed that un-reacted chloropropyltriethoxysilane compound did not remain in the product.

$^1$H-NMR 200 MHz ($D_2O$): δ3.60 ppm(q, 2H, J=7.18 Hz), 3.17–30.00 ppm(m, 20H) 1.65–1.27 ppm(br s, br s 40H), 1.13 ppm(t, 3H, J=6.92 Hz), 0.53 ppm(t, 2H, J=8.82 Hz).

Conditions of TLC analysis:

Rf value of chloropropyltriethoxysilane; 0.9 (Developing solution; n-hexane/ethyl acetate=4/1).

There is no un-reacted chloropropyltriethoxysilane compound on thin layer chromatography after completion of the reaction.

EXAMPLE IV

Antimicrobial Activity Assay of PAGS

One of the most widely used methods for quantitatively measuring the antimicrobial activity of a material is to measure, so-called, minimum inhibitory concentration, a minimum concentration necessary for the material to inhibit the growth of microorganisms. As the value of the minimum inhibitory concentration (hereinafter referred to as "MIC") is lower, the material is of better antimicrobial activity. In general, MIC is expressed in ppm.

In spite of the same material, the MIC thereof varies with the types of microorganisms because the different cell structures according to the species make the microorganisms respond to an antimicrobial material at different sensibilities.

In this example, $10^4$ cfu/ml of microorganisms was inoculated in liquid media held in a 96-multi well plate where PAGS was diluted in 2-fold series and cultured at 30° C. for 48 hours. Thereafter, MIC was measured by deciding the turbidity of the media with the naked eye whether the microorganisms grow or not.

As to the liquid media, nutrient broth (Difco) was used for bacteria, and potato dextrose broth (Difco) for fungi. As to the antimicrobial material, PAGS-1 of Example I, PAGS-2 of Example II and PAGS-3 of Example III were used.

The results are given as shown in Table 1 below.

TABLE 1

MIC of PAGS for Microorganisms

| Microorganism | Strain | PAGS-1 (ppm) | PAGS-2 (ppm) | PAGS-3 (ppm) |
| --- | --- | --- | --- | --- |
| Bacillus subtilis ATCC6633 | Gram+ | 8.0 | 8.0 | 8.0 |
| Staphylococcus aureus ATCC25923 | Gram+ | 51.2 | 25.6 | 25.6 |
| Escherichia coli ATCC25922 | Gram− | 12.8 | 6.4 | 12.8 |
| Klebsiella pneumonia ATCC8308 | Gram− | 25.6 | 25.6 | 25.6 |
| Pseudomonas aeroginosa ATCC27853 | Gram− | 6.4 | 6.4 | 6.4 |
| Proteus vulgaris NRRL B-123 | Gram− | 3.2 | 3.2 | 6.4 |
| Salmonella typhimurium KCTC1925 | Gram− | 51.2 | 51.2 | 25.6 |
| Aspergillus niger ATCC9642 | Fungi | 6.4 | 6.4 | 3.2 |
| Candida albicans ATCC10231 | Yeast | 8.0 | 8.0 | 4.0 |

EXAMPLE V

Comparison of Antimicrobial Activity Between PAGS-1 and Quaternary Ammonium Silane Salts A solution of PAGS-1 in 20% ethanol and a solution of (3-trimethoxysilyl)propyldimethyloctadecylammonium chloride in 42% methanol (DOW CORNING-5700) were pretreated in order to exclude the influence of the solvents, after which their antimicrobial activities were measured in the same manner with that of Example IV. The results are given as shown in Table 2 below.

TABLE 2

MIC of PAGS-1 and Quaternary Ammonium Silane Salt

| Microorganism | Strain | PAGS-1 (ppm) | DC-5700 (ppm) |
| --- | --- | --- | --- |
| Bacillus subtilis ATCC6633 | Gram+ | 8.0 | 512 |
| Staphylococcus aureus ATCC25923 | Gram+ | 51.2 | 1024 |
| Escherichia coli ATCC25922 | Gram− | 12.8 | 256 |
| Klebsiella pneumomia ATCC8308 | Gram− | 25.6 | 512 |
| Pseudomonas aeroginosa ATCC27853 | Gram− | 6.4 | 512 |
| Proteus vulgaris NRRL B-123 | Gram− | 3.2 | 64 |
| Salmonella typhimurium KCTC1925 | Gram− | 51.2 | 2000 |
| Aspergillus niger ATCC9642 | Fungi | 6.4 | 1024 |
| Candida albicans ATCC10231 | Yeast | 8.0 | 64 |

EXAMPLE VI

Comparison of Stability Between PAGS Antimicrobial Sol'n and Quaternary Ammonium Silane Salt A solution of PAGS-1 obtained in Example I in 20% ethanol and a solution of (3-trimethoxysilyl)propyl dimethyloctadecyl ammonium chloride in 42% methanol (DOW CORNING-5700) each were diluted 20 times with water (for example, 10 ml of solution was added with 200 ml of water). These diluted solutions were observed for turbidity and precipitation for predetrmined periods.

The grades of turbidity and precipitation were defined as follows:

| Turbidity grade | 0: clear and transparent |
| --- | --- |
| | 1: a little cloudy |
| | 2: very cloudy |
| Precipitation grade | 0: no precipitate |
| | 1: a few precipitates |
| | 2: many precipitates |

TABLE 3

Comparison of Stability in Water between PAGS Sol'n and Quaternary Ammonium Silane Sol'n

| Agent | Test | 6 hr | 12 hr | 48 hr | 7 days | 15 days | 30 days |
| --- | --- | --- | --- | --- | --- | --- | --- |
| PAGS-1 | Turbidity | 0 | 0 | 0 | 0 | 0 | 0 |
| | Precipit'n | 0 | 0 | 0 | 0 | 0 | 0 |
| DC-5700 | Turbidity | 0 | 0 | 1 | 1 | 2 | 2 |
| | Precipit'n | 0 | 0 | 1 | 1 | 1 | 2 |

EXAMPLE VII

Treatment of Materials With PAGS Antimicrobial Sol'n

A specimen was washed with 50% isopropanol for 10 min and dried. PAGS-1 in 20% ethanol was diluted with water in such a manner that the concentration of PAGS-1 would be 2%, and stirred. In this diluted solution, the specimen was dipped for 10 min, and then dehydrated. When the specimen was made from cotton, the dehydration was carried out until the weight of the wet specimen was reduced into 50%. The dehydrated specimen was dried in an oven for 30 min at a temperature which would not affect the properties of the material, for example, 70 to 150° C. The weight difference of the specimen between after the drying and before the antimicrobial treatment was 0.5 to 2%.

Alternatively, a specimen could be antimicrobially treated by spray. A 2% antimicrobial solution was sprayed on the specimen until the weight of the specimen increased up to 50%. The same drying procedure was made with it so that the weight difference of the specimen between after the drying and before the antimicrobial treatment was 0.5 to 2%.

EXAMPLE VIII

Antimicrobial Activity Assay of Specimens Treated With PAGS

A shaking flask method was used to measure the antimicrobial activity of the treated specimen. 0.75 g of each of the antimicrobially treated specimens according to Example VII and an untreated specimen (control) were placed in an Erlenmeyer flask containing 70 ml of 0.01 M phosphate buffered saline (pH 7.0) (hereinafter referred to as "PBS") and then, autoclaved at 121° C. for 15 min.

Separately, *Klebsiella pneumonia* ATCC4352, *Escherichia coli* ATCC25922 and *Staphylococuss aureus* ATCC25923 were cultured in nutrient broth (Difco) for 24 hrs with shaking. Each of the cultures was diluted with PBS to adjust the number of the bacterial cells into about $10^6$ cfu/ml. 5 ml of each of the diluted cultures was inoculated in the Erlenmeyer flasks containing the specimens and incubated at 25° C. for 2 hours while shaking was made at 250 rpm.

After the shaking incubation, the numbers of the cultured cells in the specimen flasks and the control flask were counted. Cell reduction was determined as follows:

$$\text{Cell Reduction (\%)} = \frac{B - A}{B} \times 100$$

wherein A is the number of the cells after culturing in the specimen flask; and B is the number of the cells after culturing in the control flask.

The results for cotton, rayon, polyester and nylon specimens are given as shown in Table 4 below.

TABLE 4

Antimicrobial effect of PAGS on Fiber Materials

| | Reduction Percent (%) | | | |
| --- | --- | --- | --- | --- |
| Microorganism | Cotton | Rayon | Polyester | Nylon |
| K. pneumonia ATCC4352 | 99.9 | 99.9 | 99.9 | 99.9 |
| E. coli ATCC25922 | 99.9 | 99.9 | 99.9 | 99.9 |
| S. aureus ATCC25923 | 99.9 | 99.9 | 99.9 | 99.9 |

EXAMPLE IX

Wash Fastness of Specimens Treated With PAGS

One of the conditions necessary for antimicrobial agents for fibers is that the antimicrobial agent has wash fastness. The wash fastness was measured by evaluating whether the antimicrobial activity was effected in the antimicrobially treated fiber materials after they had been washed a predetermined number of times. The fiber materials were washed in an automatic washing machine in which a cycle consisting of 22 min of wash, 12 min of rinse and 7 min of dehydration was performed at 30° C. under a ratio of water to fiber material of 30 or less, using commercially available synthetic detergent at a concentration of 0.2%. The same as in Example VIII were made with the antimicrobial activity assay, fiber materials and microbial strains. The results are given as shown in Table 5 below.

TABLE 5

Wash Fastness of PAGS-1 in Fiber Materials

| Fiber | | Cell Reduction (%) After Washing Rounds | | | | | |
| --- | --- | --- | --- | --- | --- | --- | --- |
| Material | Bacteria | 0 | 10 | 20 | 30 | 40 | 50 |
| Cotton | K. pneumonia | 99.9 | 99.9 | 99.9 | 99.9 | 99.9 | 99.9 |
| | E. coli | 99.9 | 99.9 | 99.9 | 99.9 | 99.9 | 99.9 |
| | S. aureus | 99.9 | 99.9 | 99.9 | 99.9 | 99.9 | 99.9 |
| Rayon | K. pneumonia | 99.9 | 99.9 | 99.9 | 99.9 | 99.9 | 99.9 |
| | E. coli | 99.9 | 99.9 | 99.9 | 99.9 | 99.9 | 99.9 |
| | S. aureus | 99.9 | 99.9 | 99.9 | 99.9 | 99.9 | 99.9 |
| Polyester | K. pneumonia | 99.9 | 99.5 | 95.0 | 91.0 | 85.0 | 82.0 |
| | E. coli | 99.9 | 99.9 | 99.9 | 99.0 | 95.0 | 83.0 |
| | S. aureus | 99.9 | 99.9 | 99.5 | 92.0 | 87.0 | 80.0 |
| Nylon | K. pneumonia | 99.9 | 99.9 | 97.0 | 94.0 | 86.0 | 81.0 |
| | E. coli | 99.9 | 99.9 | 99.9 | 96.0 | 88.0 | 82.0 |
| | S. aureus | 99.9 | 99.9 | 98.0 | 93.0 | 89.0 | 79.0 |

As apparent from Table 5, the cotton and rayon treated with PAGS retain their antimicrobial activities without degradation even after washing 50 times. In contrast, the wash fastness of PAGS is reduced in the case of the synthetic fibers, polyester and nylon. It is believed that such reduction is attributed to a fact that PAGS adheres to the synthetic fibers with less strength than to the natural fibers.

EXAMPLE X

Durability of PAGS to Strong Acid and Strong Alkali

After being treated with strong acid and strong alkali, the cotton and the rayon, antimicrobially treated according to Example VII, were evaluated for antimicrobial activity. This was to test for chemical resistance since fiber materials have a strong possibility of being contaminated with various acids and alkalies. 1 N hydrochloric acid and 1 N sodium hydroxide water solutions were employed. The fiber materials were immersed in the acid and alkali solutions for 1 hr and then neutralized by washing three times with 0.1 M PBS (pH 7.0). The same as in Example VIII were made with the antimicrobial activity assay and the microbial strains and the results are given as shown in Table 6 below.

TABLE 6

Acid and Alkali Resistance of PAGS-treated Fiber Materials

| Fiber Material | Bacteria | Cell Reduction (%) After Acid/Alkali Treat | |
|---|---|---|---|
| | | HCl (1 N) | NaOH (1 N) |
| Cotton | K. pneumonia | 99.9 | 99.9 |
| | E. coli | 99.9 | 99.9 |
| | S. aureus | 99.9 | 99.9 |
| Rayon | K. pneumonia | 99.9 | 99.9 |
| | E. coli | 99.9 | 99.9 |
| | S. aureus | 99.9 | 99.9 |

From Table 6, it is apparent that the PAGS applied for the fiber materials almost completely retains its antimicrobial activity against strong acid and strong alkali.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. Polyalkylene guanidine salts or polyalkylene biguanidine salts having a branched silane compound, represented by the following formula I:

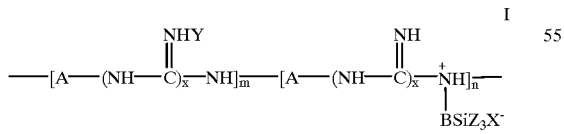

wherein A is oxyethylene, oxypropylene, oxybutylene, oxystyrene, diphenylsulfone, diphenyl sulfide or alkylamide, with a repeating number of 1 to 100,000, or straight or branched alkyl chain containing 1 to 20 carbon atoms;

Y is nothing or represents HCl, HBr, HI, $HNO_3$, acetic acid, benzoic acid, dehydroacetic acid, propionic acid, gluconic acid, sorbic acid, phosphoric acid, fumaric acid, maleic acid, carbonic acid, sulfuric acid or para-toluene sulfonic acid;

B is nothing or represents a straight or branched alkyl chain containing 1 to 20 carbon atoms;

z is an alkoxy group selected from the group consisting of methoxy, ethoxy, propoxy, isopropoxy, butoxy, pentoxy, hexoxy, octoxy or decoxy, chloride, bromide, iodide, acetate, sulfate, or paratoluenesulfonate;

X is chloride, bromide, iodide, acetate, sulfate, paratoluenesulfonate, methoxy, ethoxy, propoxy, isopropoxy, butoxy, pentoxy, hexoxy, octoxy, or decoxy;

x is 1 or 2;

m is an integer of 0 or more; and n is an integer of 1 or more with a proviso that the ratio of m to n ranges from 0.01 to 100 in the case of m+n=4 and when m is 0, n is an integer of 4 or more.

2. A process for providing antimicrobial protection to various natural and synthetic substances, which comprises:

applying polyalkylene guanidine salts or polyalkylene biguanidine salts having a branched silane compound, represented by the following Formula I as antimicrobial agents:

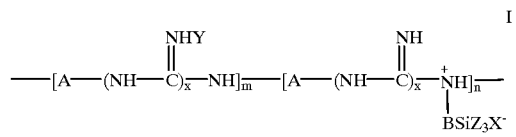

wherein A is oxyethylene, oxypropylene, oxybutylene, oxystyrene, diphenylsulfone, diphenyl sulfide or alkylamide, with a repeating number of 1 to 100,000, or straight or branched alkyl chain containing 1 to 20 carbon atoms;

Y is nothing or represents HCl, HBr, HI, $HNO_3$, acetic acid, benzoic acid, dehydroacetic acid, propionic acid, gluconic acid, sorbic acid, phosphoric acid, fumaric acid, maleic acid, carbonic acid, sulfuric acid or para-toluene sulfonic acid;

B is nothing or represents a straight or branched alkyl chain containing 0 to 20 carbon atoms;

Z is an alkoxy group selected from the group consisting of methoxy, ethoxy, propoxy, isopropoxy, butoxy, pentoxy, hexoxy, octoxy or decoxy, chloride, bromide, iodide, acetate, sulfate, or para-toluenesulfonate;

x is chloride, bromide, iodide, acetate, sulfate, para-toluenesulfonate, methoxy, ethoxy, propoxy, isopropoxy, butoxy, pentoxy, hexoxy, octoxy, or decoxy;

x is 1 or 2;

m is an integer of 0 or more; and n is an integer of 1 or more with a proviso that the ratio of m to n ranges from 0.01 to 100 in the case of m+n=4 and when m is 0, n is an integer of 4 or more.

3. The process of claim 2, wherein said antimicrobial agents are applied to synthetic fibers, natural fibers, wood, paper, glass, synthetic or natural resins, or metals.

4. An antimicrobial agent composition, comprising 0.1 to 80% by weight of polyalkylene guanidine salts or polyalkylene biguanidine salts having a branched silane compound, represented by the following formula I as an active ingredient in 99.9 to 20% by weight of water or an organic solvent having a boiling point of 25 to 300° C.:

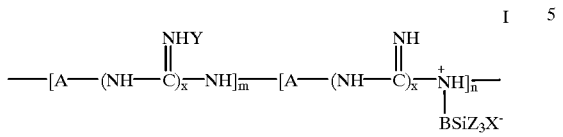

wherein A is oxyethylene, oxypropylene, oxybutylene, oxystyrene, diphenylsulfone, diphenyl sulfide or alkylamide, with a repeating number is 1 to 100,000, or straight or branched alkyl chain containing 1 to 20 carbon atoms;

Y is nothing or represents, HCl, HBr, HI, $HNO_3$, acetic acid, benzoic acid, dehydroacetic acid, propionic acid, gluconic acid, sorbic acid, phosphoric acid, fumaric acid, maleic acid, carbonic acid, sulfuric acid or para-toluene sulfonic acid;

B is nothing or represents a straight or branched alkyl chain containing 1 to 20 carbon atoms;

Z is an alkoxy group selected from the group consisting of methoxy, ethoxy, propoxy, isopropoxy, butoxy, pentoxy, hexoxy, octoxy or decoxy, chloride, bromide, iodide, acetate, sulfate, or paratoluenesulfonate;

X is chloride, bromide, iodide, acetate, sulfate, paratoluenesulfonate, methoxy, ethoxy, propoxy, isopropoxy, butoxy, pentoxy, hexoxy, octoxy, or decoxy;

x is 1 or 2;

m is an integer of 0 or more; and n is an integer of 1 or more with a proviso that the ratio of m to n ranges from 0.01 to 100 in case of m+n=4 and when m is 0, n is an integer of 4 or more.

5. The antimicrobial agent composition in accordance with claim 4, wherein said organic solvent is selected from the group consisting of a lower alcohol, an organic acid, an aromatic solvent, a polar solvent, and a halogenic solvent.

6. The antimicrobial agent composition in accordance with claim 5, wherein said organic solvent is selected from the group consisting of methanol, ethanol, propanol, butanol, pentanol, hexanol, formic acid, acetic acid, propionic acid, benzene, toluene, xylene, dimethyl sulfoxide, dimethylformamide, N-methylpyrrolidone, tetrahydrofuran, petroleum ether, dimethoxyethane, nitromethane, dichloromethane, dichloroethane, chloroform, tetrachlorocarbon and trichlorobenzene.

7. A diluted antimicrobial agent composition comprising an antimicrobial composition in accordance with claim 4 in an amount of 0.00001 to 50% by volume.

* * * * *